United States Patent [19]

Holmes

[11] 4,075,206

[45] Feb. 21, 1978

[54] SUBSTITUTED PYRROLOQUINOXALINONES AND DIONES

[75] Inventor: Richard E. Holmes, Indianapolis, Ind.

[73] Assignee: Eli Lilly and Company, Indianapolis, Ind.

[21] Appl. No.: 772,154

[22] Filed: Feb. 25, 1977

[51] Int. Cl.$^2$ .................. A61K 31/33; C07D 487/04
[52] U.S. Cl. .................. 260/250 BC; 260/250 Q; 260/239.3 T; 260/325 R; 260/326.5 B; 424/250
[58] Field of Search ...... 260/250 BC, 250 Q, 326.5 B, 260/325 R, 239.3 T

[56] References Cited

U.S. PATENT DOCUMENTS

| 3,579,503 | 5/1971 | Hester | 260/239.3 T |
|---|---|---|---|
| 3,642,821 | 2/1972 | Hester | 260/239.3 T |
| 3,813,392 | 5/1974 | Sellstedt et al. | 260/250 R |
| 3,892,746 | 7/1975 | Sellstedt et al. | 260/247.2 A |

Primary Examiner—Donald G. Daus
Assistant Examiner—James H. Turnipseed
Attorney, Agent, or Firm—James L. Rowe; Arthur R. Whale

[57] ABSTRACT

Substituted pyrroloquinoxalinones and diones, useful as anti-inflammatory and anti-thrombotic agents.

8 Claims, No Drawings

SUBSTITUTED PYRROLOQUINOXALINONES AND DIONES

BACKGROUND OF THE INVENTION

Substituted quinoxalinones are known as anti-viral and inflammatory agents: see for example, Great Britian Pat. No. 1,394,170 (Derwent Agdoc. 33957U) or Belgian Pat. No. 818,784 (Derwent Agdoc 3871W). Quinoxalinones of biological interest are also described by Acheson in *J. Chem. Soc.*, 4731 (1950). Substituted quinoxalines were suggested as anti-malarial compounds during World War II by the group working under the direction of F. H. S. Curd—see for example *J. Chem. Soc.*, 1260 (1949). Cheeseman, *J. Chem. Soc.*, 1804 (1955) has described quinoxalinones and quinoxalindiones without, however, describing any particular utility therefor. Pyrroloquinoxalines are known in the art, but a majority of these art references are to linear molecules; the three rings are in a line. For example, dodecahydropyrrolo[1,2-a]quinoxaline is mentioned in *J. Am. Chem. Soc.*, 72, 2982 (1950); 2H-pyrrolo[2,3-b]quinoxaline is mentioned in *J. Ind. Chem. Soc*, 40, 358 (1963); and 6H-pyrrolo[2,3-g]quinoxaline is described in *Bio. Chem. J.*, 69, 59 (1958). *Tetrahedron Letters*, 1969, 1581, *Angew. Chem. Int. Ed. Engl.*, 1968, 751 and *Chem. Pharm. Bull.*, 1970, 2065 also mention other linear pyrroloquinoxalines. One reference describes fused pyrroloquinoxalines; U.S. Pat. No. 3,813,392 which discloses 3H-pyrrolo[1,2,3-de]quinoxaline-2-ones, useful as central nervous system depressants.

A pyrrolo[1,2,3-ef][1,5]benzodiazepine [named as a 1,4-diazepino(3,1-h,i)indole] was prepared by Maitlis, *Proc. Chem. Soc.* 1957, 354.

SUMMARY OF THE INVENTION

This invention provides compounds of the formula:

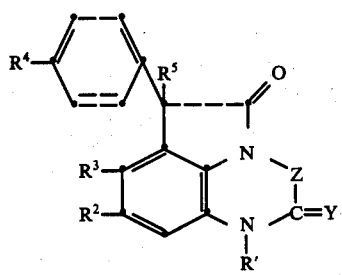

wherein R' is H or $C_1$–$C_3$ alkyl;
when taken singly, $R^2$ is H, $C_1$–$C_3$ alkyl, $C_1$–$C_3$ alkoxy, or Cl and $R^3$ is H; and
$R^2$ and $R^3$ when taken together with the carbon atoms to which they are attached form a benzene ring;
$R^4$ is H, Cl or F;
$R^5$ is OH, H or phenyl;
Y is O or $H_2$:
z is —$CH_2$—$CH_2$—or —$CHR^6$— wherein $R^6$ is H or $C_1$–$C_3$ alkyl.

When Z in Structure I is $CHR^5$, the resulting structure is a pyrroloquinoxalinone of Structure II below with the ring atoms numbered conventionally.

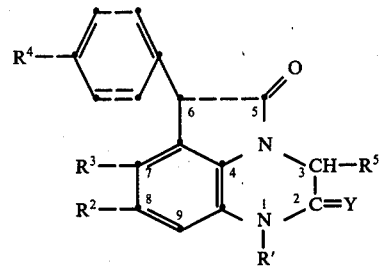

Wherein $R^1$, $R^2$, $R^3$, $R^4$ and $R^5$ and Y have the same meaning as herein above. In structure II, when Y is O, the resulting compound is a 1-substituted (or unsubstituted)-6-phenyl-1H-pyrrolo[1,2,3-de]quinoxaline-2,5]3H,6H]-dione. When Y is $H_2$, the compounds are named as 1-substituted (or unsubstituted)-6-phenyl-1H-pyrrolo[1,2,3-de]quinoxalin-5[6H]-ones.

Compounds according to Formula I above in which $R^3$ and $R^4$, when taken together with the carbon atoms to which they are attached form a benzene ring, are named as 1H-pyrrolo[1,2,3-de]benzo(g)quinoxalines. The numbering system to be employed is illustrated in Formula III below.

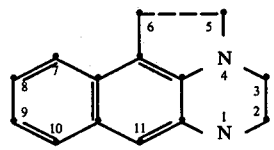

Compounds in which Z is —$CH_2$—$CH_2$ are illustrated in Formula IV below:

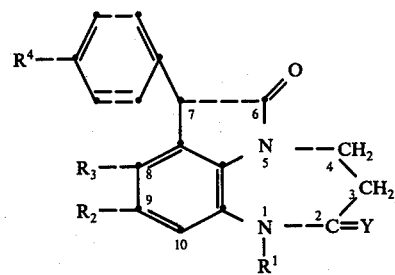

Wherein $R^1$, $R^2$, $R^3$, $R^4$ and Y have the same meaning as herein above. When Y is O, the compounds are named as 1-substituted-7-phenyl-1H-pyrrolo[1,2,3-ef][1,5]benzodiazepine-2,6(3H,7H)-diones. In the above formula, when either $R^1$ or $R^2$, or $R^5$ is $C_1$–$C_3$ alkyl, methyl, n-propyl, or isopropyl is represented. When $R^2$ is $C_1$–$C_3$ alkoxy, the following groups are represented: methoxy, ethoxy, n-propoxy, or isopropoxy.

The compounds of this invention are prepared by reacting a quinoxalinone, a quinoxaline, a benzodiazepinone, or a benzoquinoxalinone, with an α-chloro or an α-aceotxy-α (permissibly substituted)phenyl or α, α-diphenylacetyl halide. This reaction produces an amide on that quinoxaline nitrogen meta to the amide oxygen in the quinoxalinones or one of the two ring nitrogens in the tetrahydroquinoxalines. If an α-chloro acetyl derivative is formed, ring closure is effectuated with polyphosphoric acid acid to yield a pyrroloquinoxalindione. If any α-acetoxy amide is formed, the acetoxy group is preferably removed first by alkaline hydrolysis, to yield an α-hydroxy-α-phenylacetyl amide. This amide can then by cyclized as before with polyphosphoric acid to yield a pyrroloquinoxalindione or benzopyrroloquinoxalindione or pyrrolobenzodiazepinedione or the like ring system. The starting materials for the above synthetic procedures are readily available from the prior art, either being known as such or being available by the synthetic methods described therein.

Compounds containing alkyl groups at the C-3, C-8 or N-1 atoms of the quinoxaline ring system are in general prepared by a procedure which employs as starting materials, those compounds available from the prior art which have the alkyl group already in place.

Polyphosphoric acid is the condensing agent of choice employed in forming the final pyrrolo derivative, but, as will be apparent to those skilled in the art, other condensing agents can be substituted for it.

This invention is further illustrated by the following specific examples.

EXAMPLE 1

PREPARATION OF 4-DIPHENYLCHLOROACETYL-3,4-DIHYDRO-1H-QUINOXALIN-2-ONE.

A solution was prepared containing 10 g. of 3,4-dihydro-1H-quinoxalin-2-one, 9.6 g. of triethylamine in 700 ml. of benzene. A solution of 18 g. of α,α-diphenyl-2-chloroacetyl chloride dissolved in 150 ml. of benzene was added to the previous benzene solution. The resulting reaction mixture was heated at refluxing temperature for about 6 hours. A solid which separated during the reaction was separated by filtration. Removal of the solvent from the filtrate yielded as a residue 4-(α,α,-diphenyl-α-chloro)acetyl-3,4-dihydro-1H-quinoxalin-2-one formed in the above reaction. Recrystallization of this residue from benzene yielded purified material melting at 171°-2° C.; yield = 11.2 g.

Analysis Calc.: C, 70.12; H, 4.55; N, 7.43; Cl, 9.41; Found : C, 70.01; H, 4.50; N, 7.68; Cl, 9.15.

Other compounds makable by the above procedure include: 4-(p-fluorophenyl-α-chloro)acetyl-3,4-dihydro-1H-quinoxalin-2-one; mp = 128°-31° C. (from methanol).

4-(p-Chlorophenyl-α-chloro)acetyl-3,4-dihydro-1H-quinoxalin-2-one; mp = greater than 150° C. (from methanol).

Analysis Calc.: C, 58.33; H, 3.61; N, 8.36; Cl, 21.15; Found : C, 58.50; H, 4.39; N, 8.79; Cl, 20.52.

4-(α-Phenyl-α-chloro)acetyl-3,4-dihydro-1H-quinoxalin-2-one; mp = 154°-6° C.

Analysis Calc.: C, 63.90; H, 4.36; N, 9.31; O, 10.64; Cl, 11.79; Found : C, 63.70; H, 4.17; N, 9.49; O, 10.90; Cl, 11.83.

EXAMPLE 2

PREPARATION OF 6-PHENYL-1H-PYRROLO(1,2,3-de)QUINOXALINE-2,5(3H,6H)-DIONE.

About 18 g. of 4-(α-phenyl-α-chloro)acetyl-3,4-dihydro-1H-quinoxaline-2-one were mixed with 250 g. of polyphosphoric acid. The mixture was heated at about 110° C. for 5 hours and was then poured into 2000 ml. of water. A solid precipitate was separated by filtration and the filter cake washed with water. The filter cake was then dissolved in 2000 ml. of tetrahydrofurane and the resulting solution dried. The tetrahydrofurane was removed therefrom in vacuo leaving a thick red oil which was extracted with three 1500 ml. portions of hot chloroform. The chloroform extracts were combined and the chloroform removed therefrom by evaporation in vacuo. The resulting residue comprising 6-phenyl-1H-pyrrolo(1,2,3-de)quinoxaline-2,5(3H,6H)dione formed in the above reaction melted at about 235°-35° C. after being recrystallized from ethanol. A second recrystallization from chloroform yielded crystalline material melting in the range 241°-245° C., yield = 6.3 g.

Analysis Calc.: C, 71.72; H, 4.50; N, 10.60; O, 12.11; Found : C, 71.81; H, 4.35; N, 10.10; O, 12.19.

Following the above procedure, 4-(p-chlorophenyl-α-chloro)acetyl-3,4-dihydro-1H-quinoxalin-2-one was cyclized with polyphosphoric acid to yield 5-(p-chloro)phenyl-1H-pyrrolo[1,2,3-de]quinoxalin-2,5(3H,6H)-dione melting at 258°-64° C. with decomposition after recrystallization from acetone.

Analysis Calc.: C, 64.66; H, 3.71; N, 9.38; O, 10.71; Cl, 11.87; Found : C, 64.66; H, 4.00; N, 9.04; O, 10.99; Cl, 11.59.

Following the above procedure, 4-(p-fluorophenyl-α-chloro)acetyl-3,4-dihydro-1H-quinoxalin-2-one was cyclized with polyphosphoric acid to yield 6-(p-fluoro)-phenyl-1H-pyrrolo[1,2,3-de]quinoxalin-2,5(3H,6H)-dione which melted at 272°-75° C. with decomposition after recrystallization from a methanol-tetrahydrofurane solvent mixture.

Analysis Calc.: C, 68.08; H, 3.93; N, 9.92; F, 6.73; Found : C, 68.10; H, 3.67; N, 9.68; F, 6.93.

Following the above precedure, 4-(α,α-diphenyl-α-chloro)acetyl-3,4-dihydro-1H-quinoxalin-2-one was cyclized in polyphosphoric acid to yield 6,6-diphenyl-1H-pyrrolo-[1,2,3-de]quinoxalin-2,5(3H,6H)-dione which melted at 235°-55° C. with decomposition after recrystallization from methanol.

Analysis Calc.: C, 77.63; H, 4.74; N, 8.23; Found : C, 76.95; H, 6.64; N, 7.64.

EXAMPLE 3

ALTERNATE PREPARATION OF 6-PHENYL-1H-PYRROLO(1,2,3-de)-QUINOXALINE-2,5(3H,6H)-DIONE.

A mixture of 15 g. of 4-α-phenyl-α-chloroacetyl-3,4-dihydro-1H-quinoxalin-2-one in 50 g. of aluminum chloride were heated in the temperature in the range 180°-200° C. for about 30 minutes. The hot reaction mixture was poured into about 1000 g. of an ice-water mixture. The resulting solid precipitate was separated by filtration and the filter cake washed with water. Recrystallization of the filter cake from chloroform yielded 6-phenyl-1H-pyrrolo(1,2,3-de)quinoxaline-2,5(3H,6H)-dione melting at 236°-40° C., after a second recrystallization from ethanol.

Analysis Calc.: C, 72.72; H, 4.58; N, 10.60; O, 12.11; Found : C, 72.20; H, 4.47; N, 10.33; O, 12.49.

EXAMPLE 4

PREPARATION OF 1-ALKYL-6-PHENYL-1H-PYRROLO[1,2,3-de]-QUINOXALINE-2,5 (3H,6H)-DIONES.

1. 1-Methyl-1H-quinoxalin-2-one was prepared by the method of Cheeseman, J. C. S., 1804, (1955). Using the same procedure, 1-ethyl-1H-quinoxalin-2-one melting at 69°-71° C. was prepared, Analysis Calc.: C, 68.95; H, 5.79; N, 16.08; Found : C, 68.81; H, 5.55; N, 15.95, and 1-n-propyl-1H-quinoxalin-2-one melting at 33°–48° C., Analysis Calc.: C, 70.19; H, 6.43; N, 14.88; Found : C, 70.03; H, 6.20; N, 14.68.

A mixture of 9.2 g. of 1-n-propyl-1H-quinoxalin-2-one and 3 g. of 5 percent Pd/C in 200 ml. of THF were hydrogenated at 60 psi for 6 hours. The catalyst was separated by filtration and the filtrate evaporated to dryness in vacuo. The residue, comprising 1-n-propyl-3,4-dihydro-1H-quinoxalin-2-one formed in the above reaction, was crystallized from hexane and melted at 78°–80° C. (yield = 7.4 g.)

Analysis Calc.: C, 69.45; H, 7.42; N, 14.73; Found : C, 69.70; H, 7.67; N, 14.67.

1-Methyl-3,4-dihydro-1H-quinoxalin-2-one was prepared by the same procedure and was an oil as was the corresponding 1-ethyl compound.

4-($\alpha$-Phenyl-$\alpha$-chloro)acetyl derivatives of the above three 1-alkyl-3,4-dihydro-1H-quinoxalin-2-ones were prepared by the method of Example 1. 4-($\alpha$-Phenyl-$\alpha$-chloro)acetyl-1-methyl-3,4-dihydro-1H-quinoxalin-2-one melted at 108°–111° C. after recrystallization from methanol.

Analysis Calc.: C, 64.87; H, 4.80; N, 8.90; Cl, 11.26; Found : C, 64.66; H, 4.51; N, 8.69; Cl, 11.54.

4-($\alpha$-Phenyl-$\alpha$-chloro)acetyl-1-ethyl-3,4-dihydro-1H-quinoxalin-2-one melted at 119°–123° C. after recrystallization from a benzene-hexane mixture.

Analysis Calc.: C, 65.75; H, 5.21; N, 8.52; Cl, 10.78; Found : C, 65.61; H, 5.27; N, 8.53; Cl, 11.04.

4-($\alpha$-Phenyl-$\alpha$-chloro)acetyl-1-n-propyl-3,4-dihydro-1H-quinoxalin-2-one melted at 105°–108° C. after recrystallization from a benzene-hexane solvent mixture.

Analysis Calc.: C, 66,57; H, 5.59; N, 8.17; Cl, 10.34; Found : C, 66.30; H, 5.71; N, 8.10; Cl, 10.05.

Following the procedure of Example 2, each of the above 4-($\alpha$-phenyl-$\alpha$-chloro)acetyl derivatives was cyclized in the presence of polyphosphoric acid to yield the corresponding 1H-pyrrolo[1,2,3-de]quinoxaline-2,5(3H,6H)-dione. The compounds thus prepared had the following characteristics:

1-Methyl-6-phenyl-1H-pyrrolo1,2,3-de]quinoxalin-2,5(3H,6H)-dione melting at 142°–4° C. after recrystallization from ethanol.

Analysis Calc.: C, 73.37; H, 5.07; N, 10.07; Found : C, 73.34; H, 5.15; N, 10.04.

1-Ethyl-6-phenyl-1H-pyrrolo[1,2,3-de]quinoxalin-2,5(3H,6H)-dione melting at 158°–61° C. after recrystallization from a benzene-acetone solvent mixture.

Analysis Calc.: C, 73.95; H, 5.52; N, 5.58; Found C, 73.98; H, 5.54; N, 9.33.

1-n-Propyl-6-phenyl-1H-pyrrolo[1,2,3-de]quinoxalin-2,5(3H,6H)-dione melting at 147°–50° C. after recrystallization from methanol.

Analysis Calc.: C, 74.49; H, 5.92; N, 9.24; Found : C, 71.08; H, 5.65; N, 8.32.

EXAMPLE 5

PREPARATION OF 3-ALKYL-6-PHENYL-1H-PYRROLO[1,2,3-de]-QUINOCALIN-2,5(3H,6H)-DIONES.

A mixture was prepared containing 20 of 3-methyl-3,4-dihydro-1H-quinoxalin-2-one, 13.3 g. of triethylamine, and 700 ml. of benzene. The mixture was heated to refluxing temperature and 28 g. of $\alpha$-acetoxy-$\alpha$-phenylacetyl chloride in 80 ml. of benzene was added thereto. The resulting reaction was heated to refluxing temperature for about 4 hours. The solids which precipitated during this heating period were separated by filtration, and the filtrate was evaporated to dryness in vacuo. The residue comprising 4-($\alpha$-acetoxy-$\alpha$-phenyl)acetyl-3-methyl-3,4-dihydro-1H-quinoxalin-2-one formed in the above reaction was recrystallized from ethanol, melting at 215°–218° C.; yield = 19.3 g.

Analysis Calc.: C, 67.45; H, 5.36; N, 8.28; O, 19.18. Found : C, 67.73; H, 5.48; N, 8.36; O, 19.91.

A solution was prepared from 11 g. of 4-($\alpha$-acetoxy-$\alpha$-phenyl)acetyl-3-methyl-3,4-dihydro-1H-quinoxalin-2-one in 200 ml. of ethanol. 20 ml. of water and 10 ml. of 1N aqueous sodium hydroxide were added and the resulting reaction mixture heated to refluxing temperature for about 3 hours. The pH of the solution was then adjusted to about 6 with 1N aqueous hydrochloric acid. The ethanol was removed from the aqueous solution in vacuo. The aqueous solution was then extracted three times with 200 ml. portions of chloroform. The chloroform extracts were combined, dried, and the chloroform removed therefrom by evaporation in vacuo. The residue comprising 3-($\alpha$-hydroxy-2-phenyl)acetyl-3-methyl-3,4-dihydro-1H-quinoxalin-2-one formed in the above reaction was recrystallized from a benzene-hexane solvent mixture and melted below 120° C.; yield = 5.4 g.

Analysis Calc.: C, 68.91; H, 5.44; N, 9.45; O, 16.20; Found : C, 68.76; H, 5.63; N, 11.31; O, 14.86.

Following the procedure of Example 3, 4-($\alpha$-hydroxy-$\alpha$phenyl)acetyl-3,4-dihydro-1H-quinoxalin-2-one prepared in the above reaction was cyclized with polyphosphoric acid to yield 6-phenyl-3-methyl-1H-pyrrolo 1,2,3-de]quinoxalin-2,5(3H,6H)-dione melting at 208°–211° C. after recrystallization from an ethanol-hexane solvent mixture.

Analysis Calc.: C, 73.36; H, 5.07; N, 10.07; O, 11.50; Found : C, 73.13; H, 5.02; N, 10.07; O, 11.85.

Following the above series of reactions 3-ethyl-3,4-dihydro-1H-quinoxalin-2-one was reacted with ($\alpha$-acetoxy-$\alpha$phenyl)acetyl chloride to yield the corresponding 4-($\alpha$-acetoxy-$\alpha$-phneyl)acetyl derivative, the acetyl group was removed by basic hydrolysis, and the resulting $\alpha$-hydroxy derivative cyclized with polyphosphoric acid to yield 6-phenyl-3-ethyl-1H-pyrrolo[1,2,3-de]quinoxalin-2,5(3H,6H)-dione melting at 205°–208° C. after recrystallization from methanol.

Analysis Calc.: C, 73.95; H, 5.52; N, 9.50; O, 10.95; Found : C, 73.83; H, 5.32; N, 9.80;O, 11.09.

EXAMPLE 6

ALTERNATE PREPARATION OF 6-PHENYL-1H-PYRROLO[1,2,3-de]-QUINOXALIN-2,5(3H,6H)-DIONE.

Following the procedure of Example 5, 3,4-dihydro-1H-quinoxalin-2-one was reacted with ($\alpha$-acetoxy-$\alpha$-phenyl)acetyl chloride to yield 4-($\alpha$-acetoxyphenyl)acetyl-3,4-dihydro-1H-quinoxalin-2-one which melted at 156°–158° C. after recrystallization from methanol.

Analysis Calc.: C, 66.66; H, 4.91; N, 8.64; O, 19.73; Found : C, 66.57; H, 4.92; N, 8.45; O, 19.53.

The above acetoxy compound was hydrolyzed to the 4-($\alpha$-hydroxy-$\alpha$-phenyl)acetyl-3,4-dihydro-1H-quinoxalin-2-one as follows: 56 g. of 4-($\alpha$-acetoxy-$\alpha$-phenyl)acetyl-3,4-dihydro-1H-quinoxalin-2-one were dissolved in 350 ml. of methanol. 10 ml. of diisopropyl ethylamine were added and the resulting mixture refluxed for about 18 hours. The solvent was removed in vacuo and the resulting residue, comprising 4-($\alpha$-hydroxy-$\alpha$-phenyl)acetyl-3,4-dihydro-1H-quinoxalin-2-one formed in the above reaction, was recrystallized from a benzene-ethanol solvent mixture; melting point = 177°–178° C.; yield = 36.5 g.

Analysis Calc. : C, 68.08; H, 5.00; N, 9.92; O, 17.00; Found : C, 67.80; H, 4.76; N, 9.71; O, 17.27.

36 g. of the above 4-(α-hydroxy-α-phneyl)acetyl derivative was cyclized in 800 g. of polyphosphoric acid to yield 6-phenyl-1H-pyrrolo[1,2,3-de]quinoxalin-2,5(3H,6H)-dione, which had the physical characteristics previously set forth.

EXAMPLE 7

PREPARATION OF 8-SUBSTITUTED-6-PHENYL-1H-PYRROLO[1,2,3-de]QUINOXALIN-2,5(3H,6H)-DIONES.

N-(2-nitro-4-chlorophenyl)-glycine was prepared by the procedure of *J. Chem. Soc.*, 1260 (1949) and the substituted glycine cyclized to yield 7-chloro-3,4-dihydro-1H-quinoxalin-2-one utilizing a procedure also set forth in that reference. The reaction of 7-chloro-3,4-dihydro-1H-quinoxalin-2-one with α-chloro-α-phenylacetyl chloride by the procedure of example 1 yielded 4-(α-phenyl-α-chloro)-acetyl-7-chloro-3,4-dihydro-1H-quinoxalin-2-one melting at 164°–7° C. after recrystallization from methanol.

Analysis Calc.: C, 57.33; H, 3.61; N, 8.36; Cl, 21.15; Found : C, 57.14; H, 3.77; N, 8.65; Cl, 21.25.

Cyclization of this compound by the procedure of either Example 2 or Example 3 gave 6-phenyl-8-chloro-1H-pyrrolo[1,2,3-de]quinoxalin-2,5(3H,6H)-dione melting at 258°–63° C. with decomposition after recrystallization from methanol.

Analysis Calc.: C, 64.33; H, 3.71; N, 9.38; Cl, 11.87; Found : C, 64.55; H, 3.85; N, 9.25; Cl, 12.14.

Following the above procedure, 7-methoxy-3,4-dihydro-1H-quinoxalin-2-one was prepared from N-(2-nitro-4-methoxyphenyl)glycine, the latter compound being prepared according to the procedure set forth in *J. Chem. Soc.*, 1271, (1949). 4-(α-Phenyl-α-chloro)acetyl-7-methoxy-3,4-dihydro-1H-quinoxalin-2-one thus prepared melted at 156°–59° C. after recrystallization from methanol.

Analysis Calc.: C, 61.54; H, 4.86; N, 8.44; Cl, 10.69; Found : C, 61.60; H, 4.70; N, 8.67; Cl 9.11.

Cyclization of the α-chloroacetyl derivative to 6-phenyl-8-methoxy-1H-pyrrolo[1,2,3-de]quinoxalin-2,5(3H,6H)-dione was carried out according to the procedure of Example 2. The compound melted at 234°–7° C. with decomposition after recrystallization from methanol.

Analysis Calc.: C, 69.63; H, 4.79; N, 9.52; O, 16.31; Found : C, 69.26; H, 4.97; N, 9.33; O, 16.10.

Following the procedure of *J. Chem. Soc.* 1260, 1271 (1949) N-[2-nitro-4-(p-fluoro)phenyl]glycine was prepared melting at 202°–205° C. with decomposition.

Analysis Calc.: C, 44.87; H, 3.29; N, 13.08; Found : C, 45.14; H, 3.52; N, 12.94.

Cyclization to 7-fluoro-3,4-dihydro-1H-quinoxalin-2-one was carried out by the procedure of the same article. The compound melted at 214°–17° C. with decomposition after recrystallization from a benzene-THF solvent mixture.

Analysis Calc.: C, 57.83; H, 4.25; N, 16.86; F, 11.43; Found : C, 57.64; H, 4.18; N, 11.15; F, 11.15.

7-Fluoro-4(α-hydroxy-2-phenyl)acetyl-3,4-dihydro-1H-quinoxalin-2-one was prepared by the above method. It melted at 165°–7° C. after recrystallization from a benzene-methanol solvent mixture.

Analysis Calc.: C, 64.00; H, 4.36; N, 9.33; F, 6.33; Found : C, 63.76; H, 4.22; N, 9.45; F, 6.20.

The 4-acetylderivative was cyclized by polyphosphoric acid to yield 6-phenyl-8-fluoro-1H-pyrrolo[1,2,3-de]quinoxaline-2,5(3H,6H)-dione as set forth above. The compound melted at 205°–8° C. after recrystallization from benzene.

Analysis Calc.: C, 68.08; H, 3.93; N, 9.92; F, 6.73; Found : C, 68.27; H, 4.16; N, 10.08; F, 6.78.

The same sequence of reaction was carried out to prepare the 8-methyl derivatives. N-[2-Nitro-4-(p-methyl)-phenyl]glycine was prepared by the method of J. A. C. S. 1260 (1949) and melted at 184°–6° C.

Analysis Calc.: C, 51.43; H, 4.80; N, 13.30; Found : C, 51.69; H, 4.04; N, 13.57.

7-Methyl-3,4-dihydro-1H-quinoxalin-2-one prepared therefrom melted at 129°–31° C. after recrystallization from an ethanol-water solvent mixture.

Analysis Calc.: C, 66.65; H, 6.21; N, 17.27; Found : C, 66.38; H, 6.41; N, 17.19.

4-(α-Chloro-α-phenyl)acetyl-7-methyl-3,4-dihydro-1H-quinoxalin-2-one prepared therefrom was cyclized directly (without further purification) using polyphosphoric acid by the procedure of Example 2 to yield 6-phenyl-8-methyl-1H-pyrrolo[1,2,3-de]quinoxalin-2,5(3H,6H)-dione melting at 195°–200° C. with decomposition after recrystallization from ethanol.

Analysis Calc.: C, 73.37; H, 5.07; N, 10.07; Found : C, 73.17; H, 5.27; N, 9.85.

EXAMPLE 8

PREPARATION OF 6-PHENYL-1H-BENZO[g]PYRROLO[1,2,3-de]-QUINOXALIN-2,3(3H,6H)-DIONE.

A solution of 20 g. of 2,3-diaminonaphthalene in 400 ml. of ethanol was prepared. A solution of 11.6 g. of glycollic acid hydrate in 200 ml. of ethanol was added thereto and the resulting reaction mixture heated at refluxing temperature for about 4 hours. The solid quinoxalinone which precipitated upon cooling was collected by filtration and the filter cake washed with ethanol. Recrystallization of the filter cake from THF yielded 6,7-benzo-1H-quinoxalin-2-one melting at 334°–338° C. with decomposition, (yield = 12.2 g).

Analysis Calc.: C, 73.46; H, 4.11; N, 14.88; O, 8.15; Found : C, 73.15; H, 3.98; N, 14.13; O, 7.81.

A hydrogenation mixture was prepared containing 12 g. of 6,7-benzo-1H-quinoxalin-2-one, 3 g. of 5 percent of Pd/C and 270 ml. of DMF. The mixture was hydrogenated at 60 psi for 6 hours after which time the catalyst was removed by filtration and the filtrate evaporated to dryness in vacuo. 6,7-Benzo-3,4-dihydro-1H-quinoxalin-2-one thus formed remained as a residue and melted at 267°–70° C. with decomposition after recrystallization from THF. Yield = 8.3 g.

Analysis Calc.: C, 72.71; H, 5.09; N, 14.13; O, 8.07; Found : C, 72.76; H, 4.87; N, 14.34; O, 8.18.

Following the procedure of Example 1, the above quinoxalinone was reacted with α-chloro-α-phenylactyl chloride by the procedure of Example 1 to yield 4-(α-chloro-α-phenyl)acetyl-6,7-benzo-3,4-dihydro-1H-quinoxalin-2-one which melted at 198°–200° C. with decomposition after recrystallization from methanol.

Analysis Calc.: C, 64.48; H, 4.31; N, 7.99; Cl, 10.11; Found : C, 68.35; H, 4.14; N, 8.12; Cl, 9.92.

Following the procedure of Example 2, the above α-chloroacetylamide was cyclized with polyphosphoric acid to yield 6-phenyl-1H-benzo[g]pyrrolo[1,2,3-de]-quinoxalin-2,5(3H,6H)-dione which melted at 296°–300° C. with decomposition after recrystallization from THF.

Analysis Calc.: C, 76.42; H, 4.49; N, 8.91; Found : C, 76.14; H, 4.46; N, 8.87.

EXAMPLE 9

PREPARATION OF 2,3-DIHYDRO-6-PHENYL-1H-PYRROLO[1,2,3-de]-QUINOXALIN-5(6H)-ONE.

A solution was prepared containing 7 g. of 1,2,3,4-tetrahydroquinoxaline prepared by the procedure of *J. Am. Chem. Soc.*, 69, 797 (1947) and 5.2 g. of triethylamine in 750 ml. of benzene. A solution of 11.12 g. of α-acetyl-mandeloyl chloride in 100 ml. of benzene was added thereto. The resulting mixture was stirred at ambient temperature for about 6 hours. Solids which formed during the reaction were separated by filtration and the filtrate was evaporated to dryness in vacuo. The residue comprising 4-(α-acetoxy-α-phenyl)acetyl-1,2,3-tetrahydroquinoxaline formed in the above reaction was recrystallized from a benzene-hexane solvent mixture and melted at 125°–7° C. (yield = 13.2 g.).

Analysis Calc.: C, 69.66; H, 5.85; N, 9.03; Found : C, 69.59; H, 5.95; N, 8.88.

5 Gms. of 4-(α-acetoxy-α-phenyl)acetyl-1,2,3-tetrahydroquinoxaline was added to 15 ml. of 18 M sulfuric acid kept in an oil bath at about 76° C. The resulting mixture was stirred for 30 minutes and was then poured into 200 g. of ice. The pH of the resulting solution was adjusted to about 7 with 5 N aqueous sodium hydroxide. The neutral aqueous solution was extracted twice with 300 ml. of ethyl acetate. The ethyl acetate extracts were separated, combined, washed with water and dried. Removal of the ethyl acetate in vacuo yielded a residue comprising 2,3-dihydro-6-phenyl-1H-pyrrolo[1,2,3-de]-quinoxalin-5(6H)-one which melted at about 168°–71° C. after recrystallization from methanol; yield = 2.3 g.

Analysis Calc.: C, 76.78; H, 5.64; N, 11.19; O, 6.39; Found : C, 76.47; H, 5.64; N, 10.86; O, 6.85.

EXAMPLE 10

PREPARATION OF 3,4-DIHYDRO-7-PHENYL-1H-PYRROLO[1,2,3-ef]-BENZO-[f]DIAZEPINE-2,6(1H,7H)-DIONE.

3,4-Benzo(f)diazepin-2-one, prepared by the method of *J. Amer. Chem. Soc.*, 71, 1986 (1949), was reacted with α-chloro-α-phenylacetyl chloride to yield the corresponding 5-(α-chloro-α-phenyl)acetyl derivative which melted at 206°–209° C. after recrystallization from methanol.

Analysis Calc.: C, 64.87; H, 4.80; N, 8.90; O, 10.17; Cl, 11.26; Found : C, 65.07; H, 4.87; N, 9.13; O, 9.99; Cl, 11.36.

Following the procedure of Example 3, the above α-chloro-α-phenylacetyl derivative was cyclized with aluminum chloride to yield 3,4-dihydro-7-phenyl-1H-pyrrolo[1,2,3-ef](f)diazepine-2,6-(1H,7H)-dione melting at 222°–226° C. after recrystallization from methanol.

Analysis Calc.: C, 73.37; H, 5.07; N, 10.07; O, 11.50; Found : C, 73.20; H, 5.17; N, 9.97; O, 11.51

EXAMPLE 11

PREPARATION OF 6-HYDROXY-6-PHENYL-1H-PYRROLO[1,2,3-de]-QUINOXALIN-2,5(3H,6H)-DIONE.

A solution was prepared containing 235 g. of sodium sulfite and 37 g. of chloral hydrate in 600 ml. of water. A solution of 30 g. of 3,4-dihydro-1H-quinoxalin-2-one in 200 ml. of water was added thereto followed by about 30 ml. of 12 N aqueous hydrochloric acid. Next, 42 g. of hydroxylamine hydrochloride dissolved in 100 ml. of water was added thereto and the final reaction mixture was heated until refluxing temperature was achieved. The reaction mixture was then cooled in an ice bath. The solid that precipitated comprising 4-isonitrosoacetyl-3,4-dihydro-1H-quinoxalin-2-one formed in the above reaction, was separated by filtration. The filter cake was dissolved in 2000 ml. of chloroform. The chloroform solution was dried and the chloroform removed therefrom in vacuo. The resulting residue, comprising the isonitrosoacetyl derivative, was recrystallized from ethanol-benzene solvent mixture and melted at 202°–204° C.; yield = 4.2 g.

Analysis Calc.: C, 54.54; H, 4.58; N, 19.08; O, 21.80; Found : C, 54.74; H, 4.32; N, 19.09; O, 21.54.

18 ml. of 18 M sulfuric acid were heated to about 60° C. in an oil bath. 4 g. of 4-isonitrosoacetyl-3,4-dihydro-1H-quinoxalin-2-one were added thereto while maintaining the temperature in the range 60°–70° C. The resulting mixture was then heated at 80° C. for 30 minutes, after which time the reaction mixture was poured into 200 g. of ice. The solid which precipitated, comprising 1H-pyrrolo[1,2,3-de]quinoxalin-2,5,6-(3H)-trione formed in the above reaction, was separated by filtration and the filter cake washed with water. The filter cake was recrystallized from methanol yielding crystalline material melting at 294°–8° C. with decomposition.

Analysis Calc.: C, 59.41; H, 2.99; N, 13.06; O, 23.74; Found : C, 59.32; H, 3.01; N, 14.05; O, 23.44.

A suspension was prepared from 4.3 of 1H-pyrrolo[1,2,3-de]quinoxalin-2,5,6(3H)-trione in 200 ml. of THF. 16 ml. of a 2.83 M phentlmagnesium bromide solution in diethyl ether (phenyl Grignard reagent) were added thereto while maintaining the temperature in the range 10°–15° C. The resulting reaction mixture was stirred overnight after which time, 200 ml. of a saturated aqueous amonium chloride solution were added. An additional 1500 ml. of diethylether were added and the ethereal layer decanted from the solids. The ethereal layer was dried and the ether removed therefrom in vacuo. The resulting residue, comprising 6-hydroxy-6-phenyl-1H-pyrrolo[1,2,3-de]quinoxalin-2,5(3H,6H)-dione melted at 259°–62° C. with decomposition after recrystallization from methanol; yield = 2.4 g.

Analysis Calc.: C, 68.56; H, 4.32; N, 9.99; O, 17.12; Found : C, 68.29; H, 4.10; N, 10.22; O, 16.86.

The compounds of this invention are anti-inflammatory and anti-thrombotic agents. Their anti-inflammatory activity can be demonstrated by their ability to block the erythema produced by an ultra-violet light source on guinea pig skin according to the method of Windner, er al. *Arch. Int. Pharmacodyn*, 116, 261 (1958). In this procedure, albino quinea pigs weighing 225–300 gms. are shaved on the back and chemically depilated 18 to 20 hours before initiation of the test procedures.

Animals in groups of 4 are given predetermined dosages of the drug under test with one group being maintained as a control group. The drug is administered by the oral route as a suspension in 1 percent aqueous sodium carboxymethylcellulose. The control animals receive only the suspending median. After having being given the drug or suspension medium only, each group of animals is exposed to a high-intensity ultra-violet light for a predetermined period of time, the ultra-violet light being placed in contact with the depilated skin area on the animals' back. A gummed paper reinforcement is affixed to the lamp lens to provide an unexposed area of contrast for grading the light-produced erythema.

Beginning one hour after exposure and thereafter at half-hour intervals for another 1.5 hours, a trained observer grades erythema using an arbitraty scoring system based upon the degree of contrast and redness formed. The scores are weighted by factors of 4,3,2, and 1 at the 0.0, 1.5, 2.0 and 2.5 hour scoring times respectively because anti-inflammatory agents are usually less effective with the passage of time. The following scoring system is used:

| Score | Appearance of Exposed Area |
|---|---|
| 0 | No redness and no contrast |
| 1 | Slight redness with a faint reinforcement outline |
| 2 | Slight to moderate redness with a distinct outline |
| 3 | Marked redness with a distinct circular outline |

Total scores from each treatment group of four guinea pigs are compared to the control treatment, and the percent inhibition calculated as follows:

$$100 \times \frac{\left(\begin{array}{c}\text{Control} \\ \text{Score}\end{array} - \begin{array}{c}\text{Treatment} \\ \text{Score}\end{array}\right)}{\text{Control Score}} = \text{Percent Inhibition}$$

If desired, a dose-response graph can be obtained by plotting dose versus percent inhibition, each point representing the average of one treatment group of four guinea pigs. The dose ($ED_{50}$) in mg/kg cm.$^2$) which produced a 50 percent inhibition of the erythemic response for the particular compound tested can then be obtained, either directly or by extrapolation. Table I below summarizes the results obtained from testing representative compounds of the invention by the foregoing method.

Certain of the compounds of this invention are also platelet aggregation inhibitors and the results of testing for this activity are also included in Table I. The platelet aggregation test used involves the effect of a drug upon collagen-induced platelet aggregation using the method of Hermann et al., Proc. Soc. Exp. Biol. Med. 136, 548 (1972). According to this procedure, 300–400 g. guinea pigs are used and the compound is administered by the oral route in 2 doses, at time zero and again 2 hours later, at a series of graded dose levels to groups of 4 pigs each. One group is maintained as a control group. Blood is removed by heart puncture 60 minutes after the last dose, and a platelet-rich plasma prepared therefrom. A stock collagen solution is prepared by solubilizing bovine Achilles tendon with acetic acid. The stock solution contains 0.25 percent collagen, has a pH of 2.8 and is kept under refrigeration. Prior to use, 0.4 ml. of 1M aqueous sodium hydroxide is added to a 1 ml. aliquot of the stock solution, followed by further dilutions with saline (1:2 1:4, 1:8, 1:16, 1:32, etc.) A standard collagen challenge was used, 0.05 ml. of 1:45 dilution, to induce platelet aggregation and the aggregation response of the drugged guinea pigs was compared to that of the controls to determine inhibition of aggregation. The lowest active dose in mg./kg. × 2 is then determined, "active" being defined as giving about 50% inhibition of collagen-induced aggregation. (Activity was determined by computor printout with significance at the 95 percent confidence level being attained at about the 50 percent inhibition level). These lowest effective dose levels are also given in Table 1 which follows. In Table 1, column 1 gives the name of the compound, column 2, the $ED_{50}$ calculated as set forth above and column 3, the percent inhibition at a 50 mg/kg dose level where an $ED_{50}$ was not determined and column 4, the lowest active dose in the platelet aggregation test. N. A. indicates "not active" at 100 mg/kg × 2 in this latter test.

Table 1

| Name of Compound | $ED_{50}$ in mg/kg | Inhibition at 50 mg/kg dose | P.A. mg/kg × 2 |
|---|---|---|---|
| 1-methyl-6-phenyl-1H-pyrrolo-[1,2,3-de]quinoxalin-2,5(3H,6H)-dione | 4.4 | | 3.12 |
| 6-phenyl-1H-pyrrolo-[1,2,3-de]quinoxalin-2,5(3H,6H)-dione | 0.9 | | 1.56 |
| 1-ethyl-6-phenyl-1H-pyrrolo-[1,2,3-de]-quinoxalin-2,5(3H,6H)-dione | 33 | | 100 |
| 1-n-propyl-6-phenyl-1H-pyrrolo-[1,2,3-de]-quinoxalin-2,5(3H,6H)-dione | 47.5 | | |
| 6-phenyl-8-methyl-1H-pyrrolo-[1,2,3-de]-quinoxalin-2,5(3H,6H)-dione | | 51% | 3.12 |
| 6-phenyl-8-methoxy-1H-pyrrolo-quinoxalin-2,5(3H,6H)-dione | 45 | | 6.25 |
| 6-phenyl-8-chloro-1H-pyrrolo-quinoxalin-2,5(3H,6H)-dione | | 50% | 100 |
| 6-phenyl-1H-benzo[g]-pyrrolo-[1,2,3-de]-quinoxalin-2,5(3H,6H)-dione | | 42% | NA |
| 3-methyl-6-phenyl-1H-pyrrolo-quinoxalin-2,5(3H,6H)-dione | 2.5 | | 1.56 |
| 3-ethyl-6-phenyl-1H-pyrrolo-quinoxalin-2,5(3H,6H)-dione | 1.0 | | 50 |
| 6-(4-fluorophenyl)-1H-pyrrolo[1,2,3-de]-quinoxalin-2,5(3H,6H)-dione | 7.7 | | 12.5 |
| 6-(4-chlorophenyl)-1H-pyrrolo[1,2,3-de]-quinoxalin-2,5(3H,6H)-dione | | 48% | |
| 3,4-dihydro-7-phenyl-1H-pyrrolo[1,2,3-ef]-benzo-[f]-diazepin-2,6(1H,7H)-dione | 12 | | 50 |
| 2,3-dihydro-6-phenyl-1H-pyrrolo[1,2,3-de]-quinoxalin-5(3H)-one | 7.9 | | 100 |
| 6,6-diphenyl-1H-pyrrolo[1,2,3-de]-quinoxalin- | | | |

Table 1-continued

| Name of Compound | ED$_{50}$ in mg/kg | Inhibition at 50 mg/kg dose | P.A. mg/kg X 2 |
| --- | --- | --- | --- |
| 2,5-(3H,6H)-dione | 36 | | |

As anti-inflammatory agents, the compounds of this invention can be administered to mammals suffering from inflammation, either orally or parenterally, and in the case of inflammation of body surface, by topical application.

The amount of the compound or compounds employed is not critical so long as an effective, anti-inflammatory amount is used. In general, anti-inflammatory activity is exhibited at doses of from 0.01 to 50 or more mg./kg. of animal body weight.

In carrying out the anti-inflammatory methods of the present invention, it is generally preferred to employ a composition comprising the active agent and one or more adjuvants suited to the particular route of administration. Compositions for oral administration may be either solid, e.g, capsules, tablets, pills, powders, etc., or liquids, e.g., emulsions, solutions, suspensions, syrups, elixirs, etc. Inasmuch as some of the compounds to be employed as active agent are liquids, soft elastic gelatin capsules are often suitable employed for oral administration. In any of these various forms, the active agent can be combined with conventional adjuvants. In the case of solid formulations, suitable adjuvants include inert substances such as sucrose, lactose, and starch. In the case of liquid formulations, suitable adjuvants include water, mineral oil, etc. Either solid or liquid formulation can include lubricating agents, wetting agents, emulsifying and suspending agents, preserving agents, sweetening agents, flavoring agents, or perfuming agents.

In the instance of parenteral administration, the compounds of the present invention are formulated in a suitable sterile, injectable liquid.

Formulations suitable for topical administration include lotions, ointments, creams, spray, etc. Conventional adjuvants are employed.

In general, oral administration is preferred. Accordingly, a preferred formulation is a pharmaceutical preparation in dosage unit form adapted for administration to obtain an anti-inflammatory effect, comprising, per dosage unit, an effective non-toxic amount within the range from about 1 to about 1000 milligrams of one or more of the compounds or this invention. For many applications, the above preparation may suitably contain only a lesser amount of active agent, such as from about 5 to about 500 milligrams, or an even lesser amount of active agent, such as from about 25 to about 125 milligrams.

In employing those compounds of this invention which have anti-thrombotic activity in the treatment of vascular thrombosis, it should be emphasized that such treatment is customarily prophylactic in nature. Thus, there is administered to an individual an amount of drug based upon his need for such administration. In general, an individual will require treatment with an anti-thrombotic agent under either of two situations: (1) the individual already has suffered overt manifestations of a thromboembolic disease, or (2) the individual has an identifiable risk of contracting a thromboembolic disease but has not yet shown any overt manifestations of such disease. In either case, the prophylactic treatment of the individual with an anti-thrombotic agent is intended to prevent further thromboembolic disease in the individual or, at least, to minimize the effects of such disease. For prophylaxis of incipient or over thromboembolic disease, the oral route of administration is preferred, utilizing the oral dosage forms set forth above.

I claim:

1. A compound of the formula:

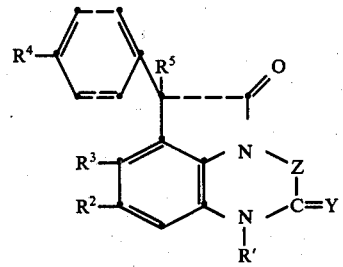

wherein
$R'$ is H or $C_1$-$C_3$ alkyl;
when taken singly, $R^2$ is H, $C_1$-$C_3$ alkyl, $C_1$-$C_3$ alkoxy, or Cl and $R^3$ is H; and
$R^2$ and $R^3$ when taken together with the carbon atoms to which they are attached form a benzene ring;
$R^4$ is H, Cl or F;
$R^5$ is OH, H or phenyl;
Y is O or $H_2$;
Z is —$CH_2$—$CH_2$—or —$CHR^6$— wherein $R^6$ is H or $C_1$-$C_3$ alkyl.

2. A compound according to claim 1 in which $R'$, $R^2$, $R^3$, $R^4$ and $R^5$ are H, Z is $CHR^6$, $R^6$ is H and Y is O, said compound being 6-phenyl-1H-pyrrolo[1,2,3-de]quinoxalin-2,5(3H,6H)-dione.

3. A compound according to claim 1 in which $R'$, $R^2$, $R^3$, $R^4$ and $R^5$ are H, Z is $CHR^6$, $R^6$ is $C_1$-$C_3$ alkyl and Y is O.

4. A compound according to claim 3 in which $R^6$ is ethyl, said compound being 3-ethyl-6-phenyl-1H-pyrrolo-[1,2,3-de]quinoxalin-2,5(3H,6H)-dione.

5. A compound according to claim 3 in which $R^6$ is methyl, said compound being 3-methyl-6-phenyl-1H-pyrrolo-[1,2,3-de]quinoxalin-2,5(3H,6H)-dione.

6. A compound according to claim 1 in which $R'$ is $C_1$-$C_3$ alkyl, $R^2$, $R^3$, $R^4$ and $R^5$ are H, Z is $CHR^6$, $R^6$ is H and Y is O.

7. A compound according to claim 6 in which $R'$ is methyl, said compound being 1-methyl-6-phenyl-1H-pyrrolo-[1,2,3-de]quinoxalin-2,5(3H,6H)-dione.

8. A compound according to claim 6 in which $R'$ is ethyl, said compound being 1-ethyl-6-phenyl-1H-pyrrolo-[1,2,3-de]quinoxalin-2,5(3H,6H)-dione.

* * * * *

UNITED STATES PATENT AND TRADEMARK OFFICE
CERTIFICATE OF CORRECTION

PATENT NO. : 4,075,206   Page 1 of 3
DATED : February 21, 1978
INVENTOR(S) : Richard E. Holmes It is certified that error appears in the above-identified patent and that said Letters Patent are hereby corrected as shown below:

Column 1, line 66, after "is" change "$CHR^5$" to --$CHR^6$--.

Column 2, in Formula II, correct the formula by attaching --$R^5$-- at carbon 6 and by changing "$R^5$" to --$R^6$-- at carbon 3.

Column 2, line 13, after "Wherein", change "$R^1$" to --R'--, after "$R^4$", insert --,$R^6$--.

Column 2, Formula IV, correct the formula by adding --$R^5$-- at carbon 7 and putting in the third double bond in the fused phenyl ring and changing "$R^1$" to --R'-- so that the corrected formula reads as follows:

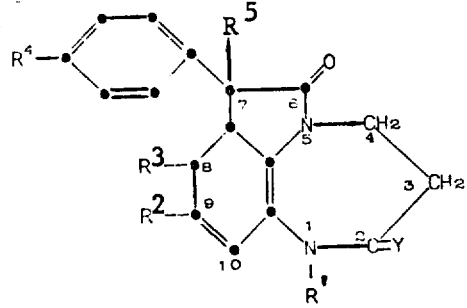

Column 2, line 49, after "Wherein", delete "$R^1$" and substitute --R', $R^5$--.

Column 2, line 53, change "formula" to --formulae--.

UNITED STATES PATENT AND TRADEMARK OFFICE
CERTIFICATE OF CORRECTION

PATENT NO. : 4,075,206

DATED : February 21, 1978

INVENTOR(S) : Richard E. Holmes

It is certified that error appears in the above-identified patent and that said Letters Patent are hereby corrected as shown below:

Column 2, line 53, change "$R^1$, $R^2$, or $R^5$" to --$R'$, $R^2$ or $R^6$--.

Column 4, line 14, change "5" to --6-- after "yield".

Column 4, line 38, "H, 6.64" should be --H, 4.64--.

Column 5, line 62, change "QUINOCALIN" to --QUINOXALIN--.

Column 6, line 29, after "acetyl" insert --3-methyl--.

Column 7, line 66, after "N", delete "11.15" and insert --16.60--.

Column 9, line 25, after "3", insert --4--.

Column 9, line 31, after "3", insert --4--.

Column 9, line 65, after "ef]" insert --[1,5]benzo--.

Column 10, line 42, after "4.3" insert --g.--.

UNITED STATES PATENT AND TRADEMARK OFFICE
CERTIFICATE OF CORRECTION

PATENT NO. : 4,075,206

DATED : February 21, 1978

INVENTOR(S) : Richard E. Holmes

It is certified that error appears in the above-identified patent and that said Letters Patent are hereby corrected as shown below:

Column 11, line 6, "medium" should be --media--.

Column 11, line 44, after "mg/kg", delete "$cm^2$)".

Columns 11-12, Table 1, in each of compounds 6, 7, 9, and 10 in the list, insert --[1,2,3-de]-- before "quinoxaline" to Signed and Sealed this Fifth Day of June 1979

[SEAL]

Attest:

RUTH C. MASON
Attesting Officer

DONALD W. BANNER
Commissioner of Patents and Trademarks